(12) United States Patent
Itamochi

(10) Patent No.: US 10,260,528 B2
(45) Date of Patent: Apr. 16, 2019

(54) CENTRIFUGAL PUMP

(71) Applicant: TERUMO KABUSHIKI KAISHA, Tokyo (JP)

(72) Inventor: Yosuke Itamochi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 406 days.

(21) Appl. No.: 15/181,696

(22) Filed: Jun. 14, 2016

(65) Prior Publication Data

US 2016/0281743 A1    Sep. 29, 2016

Related U.S. Application Data

(63) Continuation of application No. PCT/JP2014/083614, filed on Dec. 18, 2014.

(30) Foreign Application Priority Data

Dec. 27, 2013    (JP) .................. 2013-272894

(51) Int. Cl.
*F04D 29/66* (2006.01)
*A61M 1/16* (2006.01)
(Continued)

(52) U.S. Cl.
CPC .......... *F04D 29/669* (2013.01); *A61M 1/1013* (2014.02); *A61M 1/1698* (2013.01);
(Continued)

(58) Field of Classification Search
CPC ...... F04D 29/669; F04D 29/426; F04D 29/22; F04D 29/043; F04D 13/06; F04D 1/00;
(Continued)

(56) References Cited

U.S. PATENT DOCUMENTS 4,507,048 A      3/1985  Belenger et al.
4,606,698 A  *   8/1986  Clausen ................ A61M 1/101
                                                   277/328

(Continued)

FOREIGN PATENT DOCUMENTS

EP        1713159 A1     10/2006
JP        S58183080 U    12/1983
(Continued)

OTHER PUBLICATIONS

European Patent Office, European Patent Search, Reference MUB16-2122EP, Appln No. 14874234.9-1651 / 3088747 PCT/JP2014083614, dated Dec. 7, 2017.
(Continued)

*Primary Examiner* — Eldon T Brockman
(74) *Attorney, Agent, or Firm* — MacMillan, Sobanski & Todd, LLC

(57) ABSTRACT

A centrifugal pump (10) includes a housing (26), an impeller (28) that is rotatably disposed in the housing (26), a shaft (62) that is provided at a center rotational axis of the impeller (28), and bearings members (70) that respectively and pivotally support the shaft ends (66). An elastic body (80) which is elastically deformable at least in an axial direction of the shaft (62) is provided between at least one of the bearings (70) and the housing (26) or at an intermediate portion of the shaft (62) in the axial direction. A tightening load exerted on the shaft and bearing members can be maintained in a predetermined range even when age-related deformation of the housing or other components occurs.

2 Claims, 8 Drawing Sheets

(51) Int. Cl.

| | |
|---|---|
| *A61M 1/10* | (2006.01) |
| *A61M 1/26* | (2006.01) |
| *F04D 13/02* | (2006.01) |
| *F04D 29/041* | (2006.01) |
| *F04D 29/046* | (2006.01) |
| *F04D 29/22* | (2006.01) |
| *F04D 1/00* | (2006.01) |
| *F04D 13/06* | (2006.01) |
| *F04D 29/043* | (2006.01) |
| *F04D 29/42* | (2006.01) |

(52) U.S. Cl.
CPC ............... *A61M 1/267* (2014.02); *F04D 1/00* (2013.01); *F04D 13/024* (2013.01); *F04D 13/06* (2013.01); *F04D 29/041* (2013.01); *F04D 29/043* (2013.01); *F04D 29/0467* (2013.01); *F04D 29/22* (2013.01); *F04D 29/2216* (2013.01); *F04D 29/426* (2013.01); *A61M 1/101* (2013.01); *A61M 1/1006* (2014.02); *A61M 1/1012* (2014.02); *A61M 1/1036* (2014.02)

(58) Field of Classification Search
CPC .. F04D 29/2216; F04D 13/024; F04D 29/041; F04D 29/0467; A61M 1/1013; A61M 1/1698; A61M 1/267; A61M 1/1036; A61M 1/1012; A61M 1/101; A61M 1/1006
See application file for complete search history.

(56) References Cited

U.S. PATENT DOCUMENTS

| 4,898,518 | A | | 2/1990 | Hubbard et al. | |
|---|---|---|---|---|---|
| 5,575,630 | A | * | 11/1996 | Nakazawa | F04D 13/026 415/900 |
| 5,588,812 | A | | 12/1996 | Taylor et al. | |
| 5,683,231 | A | * | 11/1997 | Nakazawa | F04D 13/026 415/900 |
| 5,713,730 | A | * | 2/1998 | Nose | F04D 29/0465 417/423.12 |
| 6,123,519 | A | * | 9/2000 | Kato | A61M 1/3641 417/395 |
| 8,043,074 | B2 | * | 10/2011 | Tada | F04D 13/0666 415/123 |
| 9,662,431 | B2 | * | 5/2017 | Franano | A61M 1/3659 |
| 9,981,079 | B2 | * | 5/2018 | Scarpaci | A61M 1/288 |
| 2007/0297923 | A1 | * | 12/2007 | Tada | F04D 13/0666 417/356 |
| 2013/0165847 | A1 | * | 6/2013 | Scarpaci | A61M 1/288 604/28 |
| 2013/0338559 | A1 | | 12/2013 | Franano et al. | |
| 2015/0209498 | A1 | * | 7/2015 | Franano | A61M 1/3659 600/16 |
| 2017/0157310 | A1 | * | 6/2017 | Scarpaci | A61M 1/288 |

FOREIGN PATENT DOCUMENTS

| JP | H1198758 A | 4/1999 |
|---|---|---|
| JP | 2000297787 A | 10/2000 |
| JP | 2002085554 A | 3/2002 |
| WO | 2007063843 A1 | 7/2007 |
| WO | 2014109029 A1 | 7/2014 |

OTHER PUBLICATIONS

Japanese Patent Office Official Action dated Feb. 18, 2019.

* cited by examiner

SAMPLE B1

SAMPLE B2

SAMPLE B3

SAMPLE B4

SAMPLE B5

CENTRIFUGAL PUMP

This application is a continuation of PCT Application No. PCT/JP2014/083614, filed Dec. 18, 2014, based on and claiming priority to Japanese application no. 2013-272894, filed Dec. 27, 2013, both of which are incorporated herein by reference in their entirety.

TECHNICAL FIELD

The present invention relates to a centrifugal pump which delivers liquid such as blood and the like.

BACKGROUND ART

During cardiac surgery, a heart-lung machine is utilized. The heart-lung machine is used by being embedded in an extracorporeal circulation circuit and performs oxygenation of blood drained from a patient and filtering for elimination of foreign bodies, and the like. There are various types of heart-lung machines (also known as perfusion systems) depending on differences such as the type of gas exchange unit or oxygenator (i.e., artificial lung), the type of pump, the position where the pump is disposed, and the like. A heart-lung machine generally includes a reservoir (for venous blood), an artificial lung, a heat exchanger, a pump, and a plurality of tubes for connecting the components (for example, refer to US patent application publication US2009/0175762A1).

One type of pump adapted for use in the heart-lung machine is a centrifugal pump which delivers blood by utilizing centrifugal force occurring due to rotations of an impeller. Generally, the centrifugal pump includes a housing, wherein the impeller is rotatably disposed in the housing by a shaft which is provided at the center rotational axis of the impeller. A bearing on the housing rotatably supports the shaft. In order to reduce an occurrence of a thrombus (blood clot), a centrifugal pump may be used in which the bearing is formed as a pivot bearing.

Incidentally, in a case of the centrifugal pump employing the pivot bearing, a predetermined tightening (i.e., clamping) load is preferably applied to the shaft in the axial direction so that the shaft is rotatably supported in the housing. In this case, when the tightening load is too small, oscillations during rotations of the shaft may be increased so that hemolysis (damage to blood corpuscles) is more likely to occur. On the other hand, when the tightening load is too large, a thrombus is also more likely to occur. Therefore, it is preferable that the tightening load applied to the shaft and the bearing is set within a proper range.

Over long-term use of the centrifugal pump, the clamping load (tightening load) is continuously applied between the bearing and the housing. Therefore, there are cases where the depth of the recessed bearing surface of the bearing increases due to wear or the housing becomes warped. When a dimensional gap occurs between the members due to such deformation, the clamping load applied to the shaft and the bearing is deviated from the proper predetermined range. Accordingly, oscillations (shaft shaking) during rotations of the shaft increase so that hemolysis is more likely to occur.

SUMMARY OF INVENTION

The present invention has been made in consideration of the foregoing problem, and an object thereof is to provide a centrifugal pump in which a load applied to a shaft and bearings over long-term use can be retained within a predetermined range.

In order to achieve the object, according to the present invention, there is provided a centrifugal pump including a housing, an impeller that is rotatably disposed in the housing, a shaft that is provided at a center rotational axis of the impeller and has shaft ends at both ends thereof in an axial direction, and bearings that respectively and pivotally support the shaft ends. An elastic body which is elastically deformable at least in the axial direction of the shaft is provided between at least one of the bearings and the housing or at an intermediate portion of a segmented shaft in the axial direction.

According to the configuration of the present invention, the elastic body provided between the bearing and the housing or in the shaft causes an axial clamping load applied to the shaft and the bearing to be retained within a predetermined range. Therefore, it is possible to stably and tightly maintain the shaft between the bearings over long-term use of the centrifugal pump. In other words, even though the bearing or the housing receiving a load becomes deformed with age, the elastic body absorbs a dimensional gap which could otherwise develop between the members due to deformation. Therefore, a load applied to the shaft and the bearing is retained within a predetermined range, and oscillations of the shaft (shaft shaking) due to long-term use are prevented. Therefore, it is possible to effectively prevent an occurrence of hemolysis arising from the oscillations of the shaft.

In an embodiment of the centrifugal pump, the elastic body may be disposed between a bearing insert member and the housing. Accordingly, with a simple configuration, it is possible to absorb a dimensional gap occurring due to age-related deformation of the bearings or the housing.

In the centrifugal pump, the elastic body may preferably be disposed nearest a rear surface side of the impeller (i.e., in a lower portion or base of the housing). A space is more likely to be available on the rear surface side of the impeller than on the front surface side because of the presence of the outlet port at the upper portion of the housing. Therefore, the elastic body can be easily accommodated.

The elastic body may have a side wall which surrounds an outer circumferential portion of the bearing insert. Accordingly, the bearing can be prevented from being radially displaced toward the impeller side. Therefore, it is possible to prevent shifting of the bearing which could adversely affecting the flow of blood in the housing and to prevent the bearing from interfering with the impeller.

In a preferred embodiment of the centrifugal pump, the elastic body may be made of silicone rubber. Accordingly, it is possible to more effectively automatically compensate for age-related deformation of the bearing or the housing.

According to the centrifugal pump of the present invention, it is possible to cause a load applied to the shaft and the bearings to be kept within a predetermined range over long-term use.

DESCRIPTION OF EMBODIMENT

Hereinafter, description will be given regarding a preferred embodiment of a centrifugal pump of the present invention, with reference to the accompanying drawings.

Figure 1:
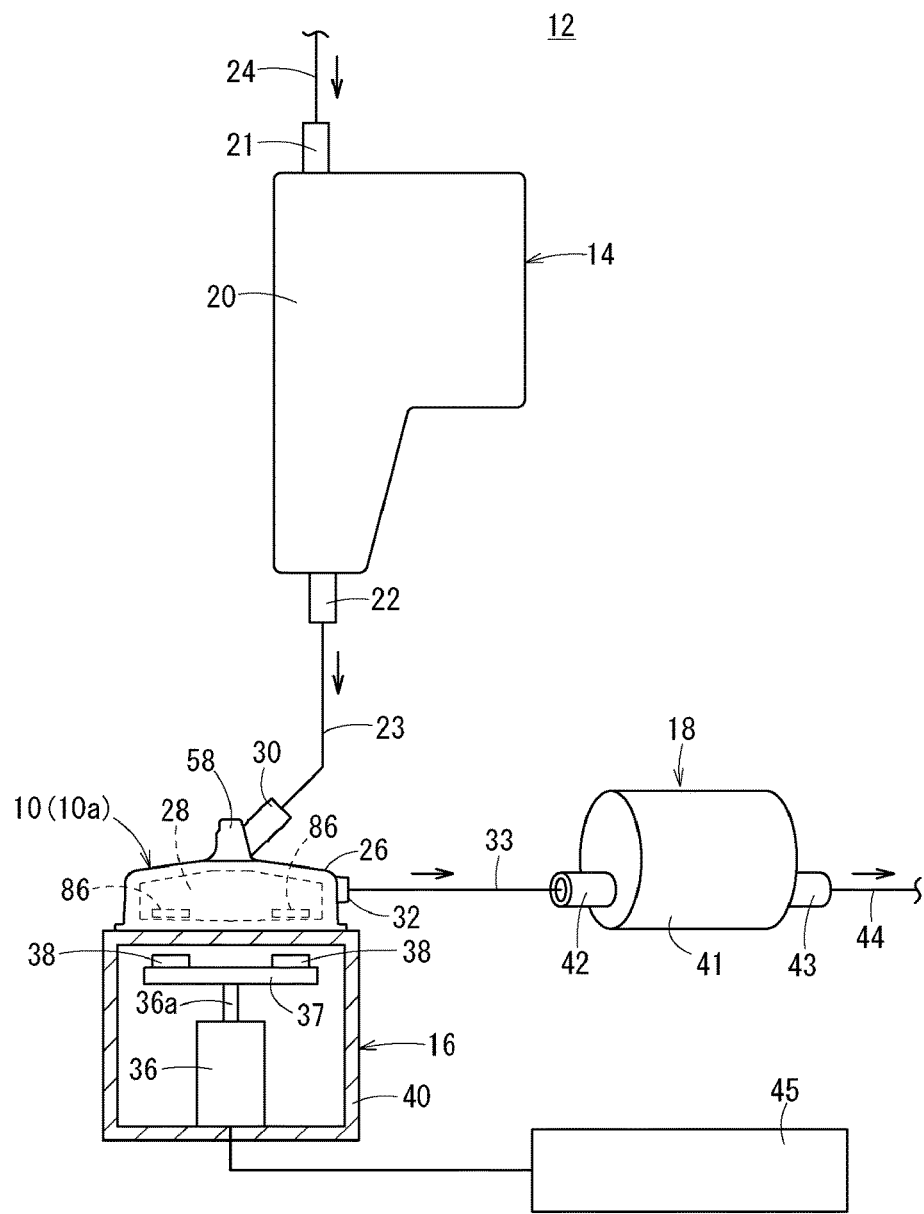
FIG. 1 is a schematic view of a heart-lung machine.

FIG. 1 is a schematic view of a heart-lung machine 12 including a centrifugal pump 10 of the present invention. For example, the heart-lung machine 12 is used for cardiac surgery or the like. The heart-lung machine 12 performs oxygenation of blood drained from a patient, filtering for elimination of foreign bodies, and the like, and then returning the blood to the patient. As illustrated in FIG. 1, the heart-lung machine 12 includes a reservoir 14, a centrifugal pump 10, a pump driving unit 16, and an artificial lung 18.

The reservoir 14 temporarily stores blood drained from a patient (venous blood). The reservoir 14 has a reservoir main body 20, a blood inlet port 21 which is provided in an upper portion of the reservoir main body 20 and is connected to a venous line 24 for delivering blood from a blood removing cannula inserted into a patient, and a blood outlet port 22 which is provided in a lower portion of the reservoir main body 20 and is connected to the centrifugal pump 10 via a first connection line 23.

In the reservoir main body 20, a blood filter (not illustrated) which filters blood flowing in via the blood inlet port 21 is disposed. Note that, the reservoir main body 20 is also provided with an inlet port (not illustrated) which is connected to a cardiotomy line for delivering blood from the surgical field of a patient.

The centrifugal pump 10 delivers blood from the reservoir 14 to the artificial lung 18. The centrifugal pump 10 includes at least a housing 26 and an impeller 28 which is rotatably disposed in the housing 26. The housing 26 has a blood inlet port 30 which is connected to the blood outlet port 22 of the reservoir 14 via the first connection line 23, and a blood outlet port 32 which is connected to the artificial lung 18 via a second connection line 33. For example, the first connection line 23 and the second connection line 33 are flexible and transparent tubes.

Blood flowing into a central portion of the impeller 28 through the blood inlet port 30 flows to an outer circumferential side of the impeller 28 while being accelerated in accordance with rotations of the impeller 28, thereby being discharged through the blood outlet port 32. Note that, the detailed structure of the centrifugal pump 10 will be described later.

The pump driving unit 16 has a motor 36, a rotary member 37 (for example, a rotary plate) which is fixed to a rotary shaft 36a of the motor 36, permanent magnets 38 which are attached to the rotary member 37, and a case 40 which accommodates these components. Preferably, a plurality of the permanent magnets 38 are provided at substantially equal intervals in the circumferential direction centering around the rotary shaft 36a of the motor 36. For example, the permanent magnets 38 are provided as many as the number of the below-described permanent magnets 86 provided in the centrifugal pump 10.

Due to the above-described configuration of the pump driving unit 16, the permanent magnets 38 provided in the pump driving unit 16 magnetically attract the permanent magnets 86 provided in the centrifugal pump 10. When the motor 36 rotates in such a magnetically attracted state, the permanent magnets 38 rotate together with the motor 36, and the impeller 28 also rotates along with the rotations thereof.

Note that, either an AC motor or a DC motor may be used as the motor 36. It is preferably to use a variable speed motor. For example, when a stepping motor is used as the motor 36, it is easy to control the flow rate of blood in the centrifugal pump 10.

The heart-lung machine 12 includes a control unit 45, and the control unit 45 controls driving of the motor 36. In the centrifugal pump 10 which is driven as described above, for example, the impeller 28 can rotate within a range from 0 rpm to 3,000 rpm. When the rotational frequency of the impeller 28 is equal to or less than 3,000 rpm, it is likely to suppress hemolysis and a thrombus from being formed. Note that, the impeller 28 may be able to rotate equal to or higher than 3,000 rpm.

The artificial lung 18 has a main body 41, a blood inlet port 42 which is connected to the blood outlet port 32 of the centrifugal pump 10 via the second connection line 33, and a blood outlet port 43 which is connected to a retransfusion line 44 for returning blood to a patient. The main body 41 adds oxygen to blood flowing in via the blood inlet port 42 and performs gas exchange for eliminating carbon dioxide. Note that, the artificial lung 18 may also have a function of heat exchange for changing a blood temperature.

Figure 2:
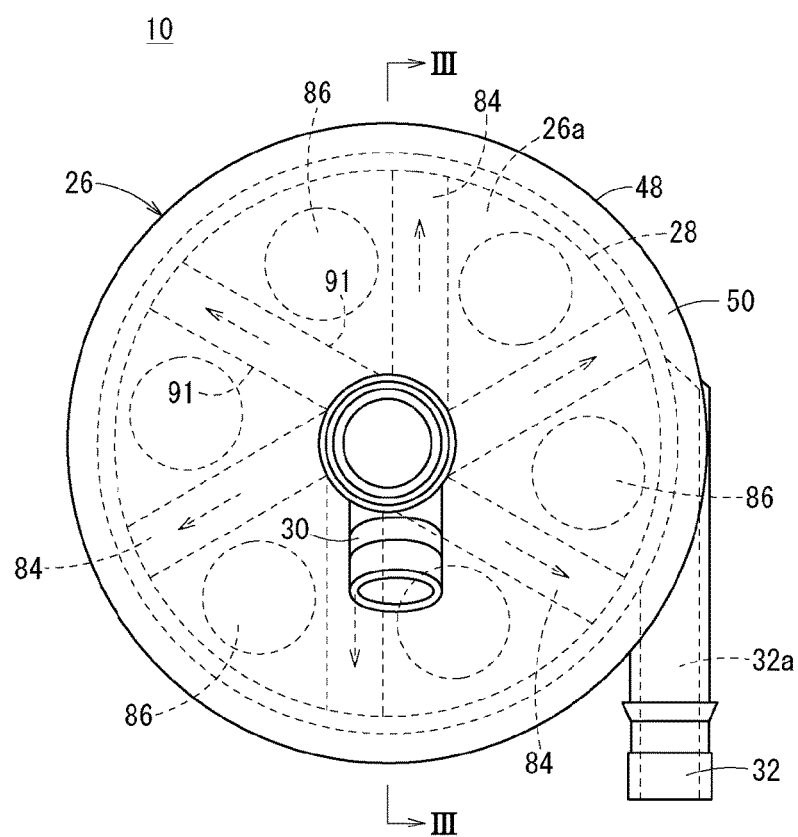
FIG. 2 is a plan view of a centrifugal pump according to an embodiment of the present invention.
Figure 3:
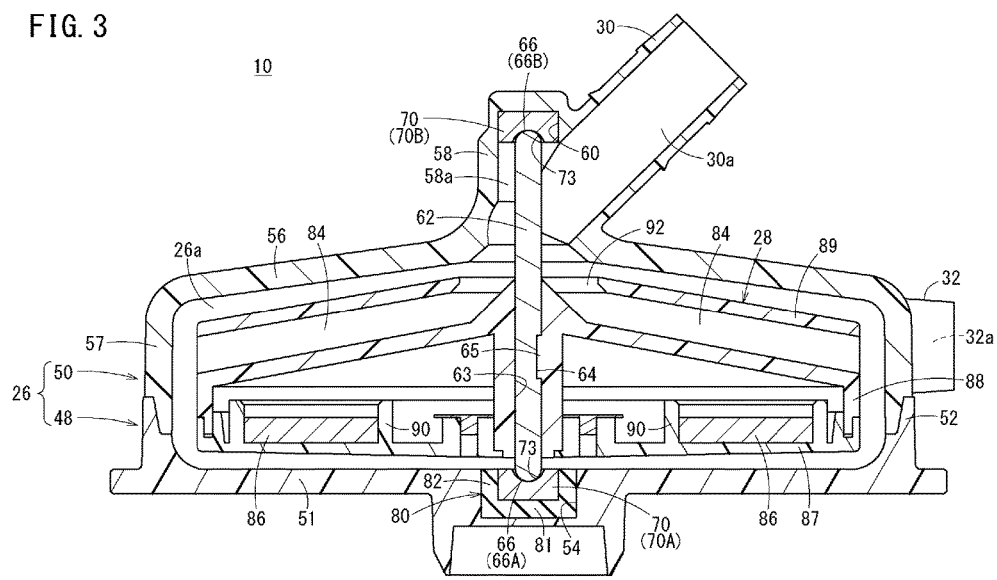
FIG. 3 is a cross-sectional view taken along line III-III in FIG. 2.

FIG. 2 is a plan view of the centrifugal pump 10. FIG. 3 is a cross-sectional view taken along line III-III in FIG. 2.

As illustrated in FIGS. 2 and 3, the housing 26 in the centrifugal pump 10 has a base 48 configuring a lower portion, and a cover 50 configuring an upper portion. The base 48 and the cover 50 having opposing internal walls creating a pumping chamber formed as a space 26a (hereinafter, referred to as "the accommodation space 26a") in which the impeller 28 is internally accommodated.

The base 48 has a substantial disk shape in its entirety. As illustrated in FIG. 3, the base 48 has a circular floor 51 and a circumferential wall 52 which protrudes upward from the outer circumferential portion of the floor 51 and continuously encircles the circumference in the circumferential direction. A central portion of the floor 51 is provided with a recessed first disposition portion (i.e., receptacle) 54.

The cover 50 has a disk-shaped ceiling 56 and a circumferential wall 57 which protrudes downward from the outer circumference of the ceiling 56 and continuously encircles the circumference in the circumferential direction. The lower end of the circumferential wall 57 of the cover 50 and the upper end of the circumferential wall 52 of the base 48 are in a state of being fitted with each other and are fixed to each other by appropriate bonding means such as an adhesive and the like. Note that, in FIG. 3, the lower end of the circumferential wall 57 of the cover 50 is fitted with the inner side of the upper end of the circumferential wall 52 of the base 48. Alternatively, the upper end of the circumferential wall 52 of the base 48 may be fitted with the inner side of the lower end of the circumferential wall 57 of the cover 50. When base 48 and cover 50 are bonded together, they impart an axial tightening load (also known as a bearing preload) to an impeller shaft via pivot bearing insert members as described below.

The cover 50 is provided with a protruding cylinder which protrudes upward from the center of the ceiling 56. The protruding cylinder portion 58 is configured to have a hollow open-bottom structure in which the upper end is closed. Inside an upper portion of the protruding cylinder portion 58, a recessed second disposition portion (i.e., receptacle) 60 is provided.

In addition, the cover 50 is provided with the above-described blood inlet port 30. In the present embodiment, the blood inlet port 30 extends from the protruding cylinder portion 58 in a direction intersecting the protruding cylinder portion 58 (in the illustrated example, in an inclination direction). A lumen 30a of the blood inlet port 30 communicates with the accommodation space 26a via a lumen 58a of the protruding cylinder portion 58.

The cover 50 is also provided with the above-described blood outlet port 32. In the present embodiment, the blood outlet port 32 extends from the outer side surface of the circumferential wall 57 of the cover 50 in a tangential direction. A lumen 32a of the blood outlet port 32 communicates with the accommodation space 26a.

As a configuration material of the housing 26 (the base 48 and the cover 50), for example, it is possible to utilize various types of resin materials such as various types of glass; polyvinyl chloride; polyethylene; polypropylene; cyclic polyolefin; polystyrene; poly-(4-methylpentene-1); polycarbonate; an acrylic resin; an acrylonitrile-butadiene-styrene copolymer; polyester such as polyethylene terephthalate, polyethylene naphthalate, and the like; a butadiene-styrene copolymer; polyamide (for example, nylon 6, nylon 6,6, nylon 6,10, nylon 12); and the like. It is preferable that the housing 26 is made of a transparent material so that blood flowing in the housing 26 can be visually recognized.

In the impeller 28, a plurality of blood induction paths 84 which radially extend from a substantial center of the impeller 28 toward the outer circumferential side are provided. In addition, inside the impeller 28, a plurality of the permanent magnets 86 for transmitting rotating force to the impeller 28 from the outside are provided at intervals in the circumferential direction. The blood induction paths 84 are not limited to being straight as illustrated in FIG. 2 and may have curved shapes.

The outer diameter of the impeller 28 is not particularly limited. For example, the outer diameter can be set to range approximately from 50 mm to 100 mm. As the outer diameter of the impeller 28 becomes greater, it is more likely to generate high discharge pressure. For example, when the outer diameter of the impeller 28 is equal to or greater than 70 mm, even though the maximum rotational frequency is approximately 3,000 rpm, it is possible to generate comparatively high discharge pressure. As described above, in a case where the rotational frequency is equal to or less than 3,000 rpm, it is likely to prevent hemolysis and a thrombus from being formed. Therefore, when the outer diameter is equal to or greater than 70 mm and the maximum rotational frequency is equal to or less than 3,000 rpm, while suppressing hemolysis and a thrombus from being formed, the impeller 28 can generate comparatively high discharge pressure.

In the present embodiment, the impeller 28 has a first rotor 87 which is configured to form the bottom portion, a second rotor 88 which concentrically overlaps the first rotor 87 from above, and a rotor cover 89 which concentrically overlaps the second rotor 88 from above.

The plurality of above-described permanent magnets 86 are respectively held by a plurality of magnet holding portions 90 which are provided on the top surface of the first rotor 87. The plurality of above-described blood induction paths 84 are formed between the second rotor 88 and the rotor cover 89.

A plurality of flow channel forming walls 91 which protrude downward from the bottom surface of the rotor cover 89 are configured to form both side walls of the blood induction paths 84. The top surface of the rotor cover 89 has a conical shape, and an opening 92 is formed in a central portion thereof.

A shaft 62 is provided at the central rotational axis of the impeller 28. The shaft 62 is a straight rod-shaped member and has spherically-shaped shaft ends 66 at opposite axial ends. The shaft 62 is fixed to the impeller 28 in a state of being inserted into the insertion hole (i.e., bore) 63 penetrating the central axial portion of the impeller 28 in the axial direction. The shaft 62 and the impeller 28 cannot relatively rotate and are fixed to each other in a state of not being able to be relatively displaced in the axial direction. In the present embodiment, a projection 65 which is provided on the inner circumferential wall forming the insertion hole 63 of the impeller 28 engages with a matching groove 64 which is provided in the shaft 62. Thus, the shaft 62 and the impeller 28 are fixed to each other.

The opposing ends of the shaft 62 respectively protrude downward and upward from the impeller 28. Hereinafter, to discriminate the two shaft ends 66 from each other, the shaft end 66 on the lower side is referred to as "the first shaft end 66A" and the shaft end 66 on the upper side is referred to as "the second shaft end 66B".

For example, the constituent material of the shaft 62 can be selected from the materials exemplified above as the configuration material of the housing 26. For example, it is preferable that the shaft 62 is to be formed from a ceramic-based material such as alumina ceramic and the like being excellent in abrasion resistance and sliding properties and being advantageous to suppress an occurrence of hemolysis and formation of a thrombus.

The centrifugal pump 10 also includes bearings 70 which are provided for opposite ends of the shaft 62 and respectively and pivotally support the shaft ends 66. Hereinafter, in a case of discriminating the two bearings 70 from each other, the bearing on the lower side, that is, the bearing pivotally supporting the first shaft end 66A is referred to as "the first bearing 70A", and the bearing on the upper side, that is, the bearing pivotally supporting the second shaft end 66B is referred to as "the second bearing 70B". In other words, the first bearing 70A and the second bearing 70B are configured to be pivot bearings. Furthermore, bearings 70A and 70B are constructed as separate members for insertion into respective upper and lower receptacles of the housing in order to provide a material with higher abrasion resistance and lower sliding friction at the interface with the rotating shaft ends.

The shaft 62 is rotatably held between the first bearing 70A and the second bearing 70B in a state where a predetermined tightening load is applied in the axial direction in the housing 26. The tightening load corresponds to a clamping force exerted by housing 26 which generates an axial "bearing preload." In a case where the tightening load is excessively small (for example, in a case of being smaller than 30 N), oscillations during rotations of the shaft 62 increase so that hemolysis is likely to occur.

Figure 5:
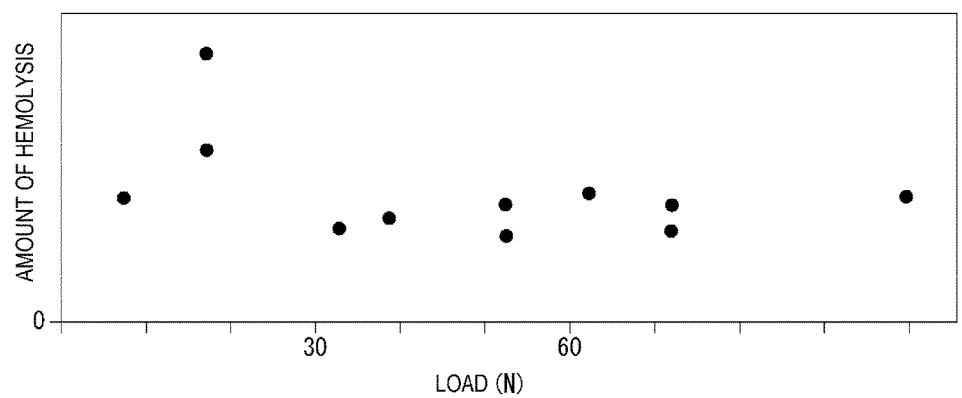
FIG. 5 is a graph illustrating a relationship between tightening loads and amounts of hemolysis.

FIG. 5 is a graph illustrating relationships between the tightening loads and amounts of hemolysis, obtained through a test. As seen from FIG. 5, in a case where the tightening load is less than 30 N, compared to a case of being equal to or more than 30 N, it is ascertained that the amount of hemolysis increases remarkably.

On the other hand, in a case where the tightening load with respect to the shaft 62 is excessive (for example, in a case of exceeding 60 N), a thrombus is likely to occur, and there is a possibility of damage to a bonded portion between the base 48 of the housing 26 and the cover 50. Therefore, it is preferable that the tightening load applied to the shaft 62 is set within a proper range (for example, approximately from 30 N to 60 N) when manufacturing the centrifugal pump 10.

As illustrated in FIG. 3, the first bearing 70A has a bearing surface 73 which is recessed so as to have a spherical surface shape. The bearing surface 73 of the first bearing 70A abuts against the first shaft end 66A. A radius r2 of curvature of the bearing surface 73 of the first bearing 70A is greater than a radius r1 of curvature of the first shaft end 66A (refer to FIG. 4).

An elastic body 80 which is elastically deformable at least in the axial direction of the shaft 62 is disposed between the bearing 70 (e.g., the first bearing 70A in the illustrated example) and the housing 26 (the base 48 in the illustrated example). The elastic body 80 is disposed (mounted or fitted) in the recessed first disposition portion 54 formed in the base 48, preferably on the rear surface side of the impeller 28. The elastic body 80 disposed as described above elastically supports the first bearing 70A. In other words, in a state where a predetermined tightening load is applied to the shaft 62 in the housing 26 and the shaft 62 is supported by the first bearing 70A and the second bearing 70B therebetween, the elastic body 80 is held in an elastic compression state between the first bearing 70A and the housing 26 (the base 48).

Figure 4:
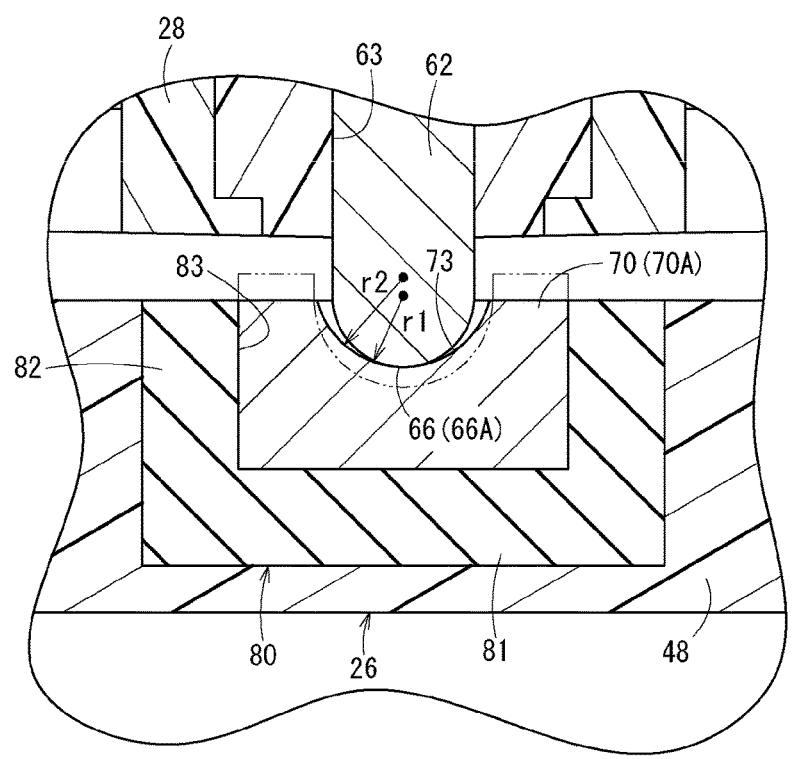
FIG. 4 is a cross-sectional view of a first bearing insert member and a peripheral portion thereof.

In the case of the present embodiment, as illustrated in FIG. 4, the elastic body 80 includes a base portion 81 and a side wall 82. The base portion 81 is clamped between the rear surface side (the opposite side of the bearing surface 73) of the first bearing 70A and the housing 26 (the base 48). The base portion 81 supports the rear surface side of the first bearing 70A. The side wall 82 which perpendicularly protrudes from an outer end of the base portion 81 and surrounds the outer circumferential portion of the first bearing 70A. The first bearing 70A which is disposed at a recessed portion 83 formed by the base portion 81 and the side wall 82 is elastically supported in the axial direction by the base portion 81 of the elastic body 80 and is elastically supported in a radial direction by the side wall 82 of the elastic body 80. Note that, the side wall 82 may be formed so as to continuously encircle the circumference in the circumferential direction, or a plurality thereof may be formed at substantially equal intervals in the circumferential direction.

In the case of the present embodiment, the elastic body 80 is made of a material having elasticity itself. As the material thereof, without being particularly limited, for example, it is possible to utilize various types of rubber materials such as natural rubber, butyl rubber, isoprene rubber, butadiene rubber, styrene-butadiene rubber, and silicone rubber; various types of thermoplastic elastomers such as a polyurethane-based elastomer, a polyester-based elastomer, a polyamide-based elastomer, an olefin-based elastomer, a styrene-based elastomer, and the like; and a mixture thereof. Among thereof, for example, silicone rubber can effectively absorb the below-described error occurring due to age-related deformation of the bearing 70 or the housing 26. Therefore, it is preferable to use silicone rubber as the material of the elastic body 80.

As illustrated in FIG. 3, the second bearing 70B has a different bearing surface 73 which is recessed so as to have a spherical surface shape. The bearing surface 73 of the second bearing 70B abuts against the second shaft end 66B, and the radius of curvature thereof is greater than the radius of curvature of the second shaft end 66B. The radius of curvature of the second shaft end 66B may be the same as or different from the radius r1 of curvature (refer to FIG. 4) of the first shaft end 66A. The radius of curvature of the bearing surface 73 of the second bearing 70B may be the same as or different from the radius r2 of curvature (refer to FIG. 4) of the bearing surface 73 of the first bearing 70A. The second bearing 70B is disposed in the recessed second disposition portion 60 which is provided in the protruding cylinder portion 58 of the cover 50.

For example, the constituent material of the bearings 70 can be selected from the materials exemplified above as the configuration material of the housing 26. It is preferable that the configuration material of the bearings 70 is made of polyethylene having an ultra-high molecular weight and being excellent in abrasion resistance and self-lubrication properties.

In the centrifugal pump 10 having the above-described configuration, when blood flows into the housing 26 via the blood inlet port 30, the blood flows into the impeller 28 through the opening 92 provided at the apex portion of the impeller 28, thereby being scattered. Centrifugal force is applied to the scattered blood due to rotations of the impeller 28 so that the blood flows in the blood induction paths 84 toward the outer circumferential side of the impeller 28. The blood flowing out from the blood induction paths 84 flows between the outer side surface of the impeller 28 and the inner side surface of the housing 26. Thereafter, the blood flows out through the blood outlet port 32.

The centrifugal pump 10 according to the present embodiment basically has a configuration as described above. Hereinafter, an operation and an effect thereof will be described.

As described above, in the centrifugal pump 10 according to the present embodiment, the elastic body 80 which is elastically deformable in the axial direction of the shaft 62 is provided. According to such a configuration, the elastic body 80 causes a load applied to the shaft 62 and the bearings 70 to be retained within a predetermined range. Therefore, it is possible to stably and tightly maintain the shaft 62 between the bearings 70 over long-term use of the centrifugal pump 10. In other words, even though the bearing 70 or the housing 26 receiving a load deforms over time in response to the load, the elastic body 80 absorbs a dimensional gap which can occur between the members due to deformation. Therefore, a load applied to the shaft 62 and the bearing 70 is retained within a predetermined range. Accordingly, oscillations of the shaft 62 (shaft shaking) due to long-term use are suppressed. Therefore, it is possible to effectively suppress an occurrence of hemolysis arising from the oscillations of the shaft 62.

Particularly, in the case of the present embodiment, the elastic body 80 is disposed between the bearing insert 70 and the housing 26. Therefore, with a simple configuration, it is possible to absorb a dimensional gap occurring due to age-related deformation of the bearing 70 or the housing 26.

In addition, as seen from FIG. 3, in a case where the elastic body 80 is disposed on the rear surface side of the impeller 28 (that is, the first bearing 70A side), a space is more likely to be provided on the rear surface side of the impeller 28 than on the front surface side. Therefore, the elastic body 80 can be easily accommodated. Note that, the elastic body 80 may be disposed on the front surface side of the impeller 28 (that is, the second bearing 70B side), and a pair of elastic bodies 80 may be disposed or fitted on both the rear surface side and the front surface side of the impeller 28 simultaneously. In this case, the elastic body 80 which is disposed on the front surface side of the impeller 28 is disposed or fitted with substantially no clearance between the second bearing 70B and the cover 50 (the protruding cylinder portion 58 in FIG. 3) of the housing 26, thereby elastically supporting the second bearing 70B.

Moreover, in the case of the present embodiment, as illustrated in FIG. 4, the elastic body 80 has the side wall 82 surrounding the outer circumferential portion of the bearing 70. Therefore, it is possible to prevent the bearing 70 from being deformed toward the impeller 28 side. In other words, in a case where the outer circumferential portion of the bearing 70 is surrounded by a hard wall replacing the side wall 82, as indicated by the virtual line in FIG. 4, in accordance with the bearing 70 being deformed during its lifetime in a direction in which a recess of the bearing surface 73 becomes greater, there is a possibility that the extra volume created by the deformation protrudes toward the impeller 28 side. In contrast, in a case where the elastic body 80 is provided with the side wall 82, in accordance with deformation in the direction in which the recess of the bearing surface 73 becomes greater, the side wall 82 absorbs the radially outward deformation of the bearing 70. Therefore, it is possible to prevent the deformed bearing 70 from adversely affecting the flow of blood in the housing 26 and to prevent the bearing 70 from interfering with the impeller 28.

In the above-described centrifugal pump 10, the elastic body 80 is provided between any one or both of the first bearing 70A and the second bearing 70B, and the housing 26. However, as in a centrifugal pump 10a according to an alternative embodiment illustrated in FIG. 6, an elastic body 94 may be provided at an intermediate portion of the shaft 62 in the axial direction. In this case, the shaft 62 includes a first shaft portion 62a and a second shaft portion 62b which respectively have the first shaft end 66A and the second shaft end 66B and are made of a hard material, and the elastic body 94 is provided between the first shaft portion 62a and the second shaft portion 62b. The elastic body 94 is interposed between the first shaft portion 62a and the second shaft portion 62b in an elastic compression state as a result of the tightening load. The configuration material of the elastic body 94 can be selected from the materials exemplified above as the configuration material of the elastic body 80.

In addition, the first shaft portion 62a is fixed to the impeller 28, and the second shaft portion 62b is not fixed. Therefore, the second shaft portion 62b can move in the axial direction as much distance as the deformation of the elastic body 94. In this case, it is preferable that a joint portion between the second shaft portion 62b and the elastic body 94 is located inside the impeller 28 (in other words, it is preferable that the elastic body 94 is disposed so as not to be exposed from the impeller 28).

Moreover, even in a case where the second shaft portion 62b moves in the axial direction as much distance as the deformation of the elastic body 94, it is preferable that the joint portion between the second shaft portion 62b and the elastic body 94 is located inside the impeller 28 so that at least a portion of the second shaft portion 62b is held at all times by a lumen provided at the center of the impeller 28 (in other words, even in a case of being deformed in the axial direction as much distance as a length released from an elastic compression state, it is preferable that the elastic body 94 is disposed so as not to be exposed from the impeller 28). Accordingly, it is possible to suppress the possibility of disconnection or folding (i.e., bending) of the shaft 62 occurring due to stress concentration and the like at the joint portion between the second shaft portion 62b and the elastic body 94.

In addition, since the second shaft portion 62b is not fixed to the impeller 28, there is a possibility of an occurrence of torsion (i.e., twisting of the shaft) starting from the elastic body 94. Therefore, it is more preferable to have a torsion prevention mechanism (not illustrated) as a prevention measure thereof, for example, forming a slit in the axial direction of the second shaft portion 62b, causing the impeller 28 to be provided with a projection portion which is fitted with the slit of the second shaft portion 62b, and the like for restricting rotations while not restricting movement in the axial direction.

Figure 6:
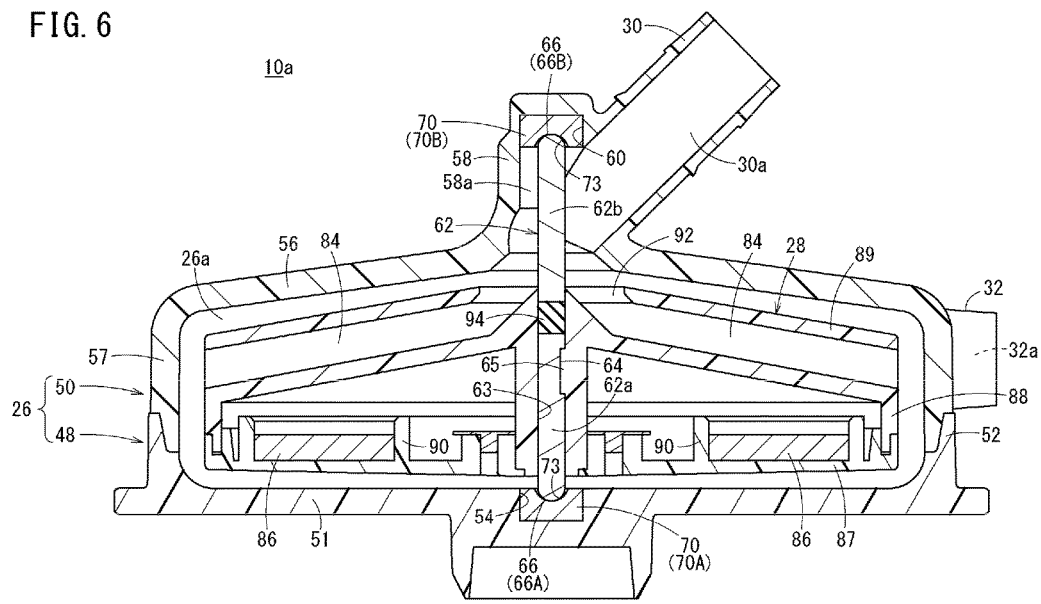
FIG. 6 is a cross-sectional view of a centrifugal pump according to an alternative embodiment.

According to the configuration of the centrifugal pump 10a of FIG. 6 as well, similar to the above-described centrifugal pump 10, the elastic body 94 provided at the intermediate portion of the shaft 62 in the axial direction causes a load applied to the shaft 62 and the bearing 70 to be retained within a predetermined range. Therefore, it is possible to stably and tightly maintain the shaft 62 between the bearings 70 over long-term use of the centrifugal pump 10a. Accordingly, oscillations of the shaft 62 (shaft shaking) due to long-term use are suppressed. Therefore, it is possible to effectively suppress an occurrence of hemolysis arising from the oscillations of the shaft 62.

Note that, in the centrifugal pump 10 and the centrifugal pump 10a, the elastic bodies 80 and 94 are not limited to one made of an inherently elastic material. Therefore, for example, the elastic bodies 80 and 94 may be bodies such as springs (coil springs, leaf springs, air springs, and the like) which are configured to have elasticity due to a mechanical structure. Furthermore, the elastic body or bodies can be placed at any suitable position between the housing walls along the linked structure formed by the shaft and bearing member, so that an elastic body is involved in transmitting the tightening load between the housing walls.

In the centrifugal pump 10, the centrifugal pump 10a, and other modifications thereof, the shaft ends 66 may be set to have surface roughness Ra (arithmetic average roughness) equal to or less than 0.21 μm, and the shaft ends 66 may be set to have surface roughness Ry (maximum height) equal to or less than 1.49 μm. In a case of such a configuration, it is possible to further suppress hemolysis from occurring due to sliding between the shaft 62 and the bearing 70, and it is possible to suppress a thrombus from being formed at the shaft ends 66 of the shaft 62. Each of the shaft ends 66 may be set to have the surface roughness Ra equal to or less than 0.21 μm or the surface roughness Ry equal to or less than 1.49 μm.

In order to check a hemolysis suppressing effect and a thrombus suppressing effect obtained by setting the surface roughness, two types of tests (a test related to an occurrence of hemolysis and a test related to formation of a thrombus) have been executed. In each test, the test was performed while having the shafts of Samples A1 to A5 as targets in which the surface roughness Ra and the surface roughness Ry of the shaft end were formed as those in Table 1. Note that, the surface roughness was measured by using a stylus-type surface roughness measuring machine (manufactured by Mitutoyo Corporation).

TABLE 1

| | Surface Roughness Ra | Surface Roughness Ry | Amount of Hemolysis | Formation of Thrombus |
|---|---|---|---|---|
| Sample A1 | 0.05 | 0.28 | Small | No |
| Sample A2 | 0.18 | 1.31 | Small | No |
| Sample A3 | 0.21 | 1.49 | Small | No |
| Sample A4 | 0.30 | 2.04 | Great | Present |
| Sample A5 | 0.44 | 2.97 | Great | Present |

In the test related to an occurrence of hemolysis, while circulating 2.0 L of blood at a flow rate of 8.0 L per minute by using a centrifugal pump in which the test target shafts were applied, the shaft (and the impeller) was continuously rotated for six hours at a rotational frequency of 2,600 rpm. The blood temperature was controlled so as to be at 37° C.

Figure 7:
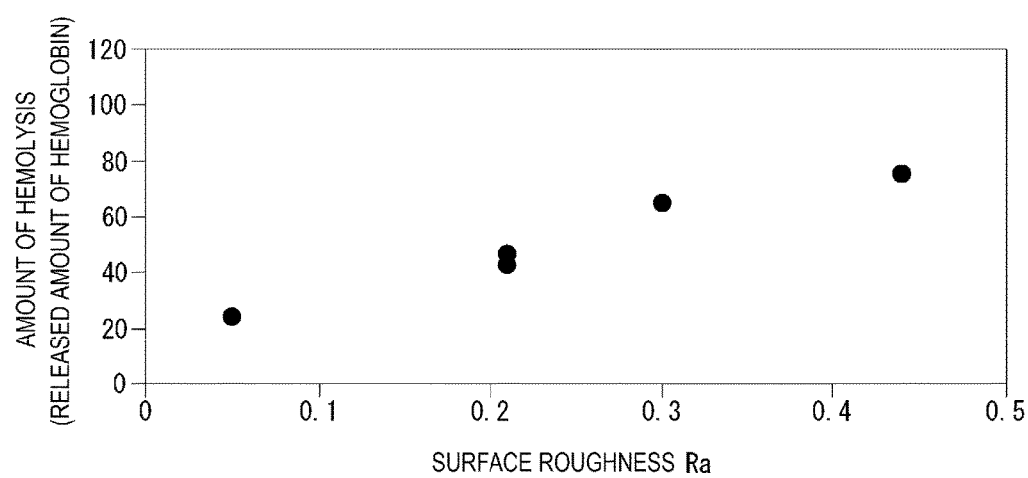
FIG. 7 is a graph illustrating relationships between surface roughness Ra (arithmetic average roughness) and the amounts of hemolysis.

FIG. 7 is a graph illustrating the test result related to an occurrence of hemolysis (relationships between the surface roughness Ra and amounts of hemolysis). As seen from FIG. 7, it is ascertained that as the surface roughness Ra of the shaft end of the shaft becomes smaller, the amount of hemolysis decreases (also refer to the column of "Amount of Hemolysis" in Table 1). In this manner, in Samples A1 to A3, compared to Samples A4 and A5, it was confirmed that the amount of hemolysis decreased. Note that, since the surface roughness Ra and the surface roughness Ry have a constant correspondence relationship, it is possible to mention that as the surface roughness Ry becomes smaller, the amount of hemolysis decreases.

In the test related to formation of a thrombus, 3 mL (heparin final concentration: 0.5 unit/mL) of blood and the test target shaft were caused to sink in a centrifugation tube, and the centrifugation tube was rotated about the central axial line of the centrifugation tube for six hours at room temperature at a predetermined speed, in a state where the centrifugation tube was laid sideways. Thereafter, the presence and the absence, and the degree of a thrombus formed at the shaft end of the shaft were checked.

As a result of the test, in Sample A1 (Ra=0.05 μm), almost no adhering blood component (platelet or the like) was found and no thrombus was confirmed. In each of Sample A2 (Ra=0.18 μm) and Sample A3 (Ra=0.21 μm), it was confirmed that a thin net-like film was slightly formed at the shaft end. Note that, the thin net-like film confirmed in Samples A2 and A3 was not a substance which might be referred to as a fibrin net (fibrin which is a fiber component in blood and is bonded in a mesh pattern), and no thrombus was confirmed. Therefore, it is understood that, in Samples A1 to A3, there is an effect of suppressing a thrombus from being formed (also refer to the column of "Formation of Thrombus" in Table 1).

Meanwhile, in Sample A4 (Ra=0.30 μm), it was confirmed that a thin fibrin net was formed at the shaft end. In Sample A5 (Ra=0.44 μm), it was confirmed that a thick fibrin net was formed at the shaft end. A thrombus is formed due to blood corpuscles or platelets which become entangled with a fibrin net. Therefore, it is understood that, in Samples A4 and A5, there is no effect of suppressing a thrombus from being formed.

According to the test result hereinbefore, it is ascertained that when the surface roughness Ra of the shaft end of the shaft is equal to or less than 0.21 μm, there is an effect of suppressing a thrombus from being formed, and as the surface roughness Ra becomes smaller, there is a high effect of suppressing a thrombus from being formed. Note that, since the surface roughness Ra and the surface roughness Ry have a constant correspondence relationship, it is possible to mention that as the surface roughness Ry becomes smaller, there is a high effect of suppressing a thrombus from being formed.

As it is understood from above, in a case where the surface roughness Ra of the shaft end 66 of the shaft 62 is equal to or less than 0.21 μm (the surface roughness Ry is equal to or less than 1.49 μm), it is possible to suppress hemolysis from occurring due to sliding between the shaft 62 and the bearing 70, and it is possible to suppress a thrombus from being formed at the shaft ends 66 of the shaft 62. Particularly, when the surface roughness Ra of the shaft end 66 is equal to or less than 0.21 μm and the surface roughness Ry of the shaft end 66 is equal to or less than 1.49 μm, an effect of suppressing an occurrence of hemolysis and formation of a thrombus is more favorably achieved.

In the centrifugal pump 10 which employs the pivot bearing insert members (the bearings 70) as means for supporting rotations of the shaft 62, the rotations of the shaft 62 are considered to be a cause of damage to blood. Therefore, controlling the surface roughness of the shaft end 66 of the shaft 62 leads to controlling of damage to blood. It is considered that formation of a thrombus or an occurrence of hemolysis arising from rotations of the shaft 62 occurs due to ground blood corpuscles, heat generation, shearing stress, and the like caused by friction between the shaft 62 and the bearing 70. It is possible to effectively exclude the above-described factors of formation of a thrombus or an occurrence of hemolysis by setting the surface roughness of the shaft end 66 of the shaft 62 within the above-referenced range.

In addition, in each of the first shaft end 66A and the second shaft end 66B, in a case where the surface roughness Ra is equal to or less than 0.21 μm (the surface roughness Ry is equal to or less than 1.49 μm), it is possible to suppress an occurrence of hemolysis and formation of a thrombus at both ends of the shaft 62. Therefore, it is possible to further enhance a hemolysis prevention effect and a thrombus prevention effect.

In addition, in a case where the shaft 62 is made of alumina ceramic, together with a hemolysis suppressing effect and a thrombus suppressing effect described above and obtained by setting the surface roughness Ra or the surface roughness Ry of the shaft end 66 of the shaft 62, it is possible to more effectively suppress hemolysis from occurring and to prevent a thrombus from being formed.

Note that, the surface roughness Ra or the surface roughness Ry of only one between the first shaft end 66A and the second shaft end 66B may be set within the above-referenced range. In this case, in any one between the first shaft end 66A and the second shaft end 66B, it is possible to obtain a hemolysis suppressing effect and a thrombus suppressing effect described above.

In the centrifugal pump 10, the centrifugal pump 10a, and other modifications thereof, both the ratio of the radius r1 of curvature of the first shaft end 66A with respect to the radius r2 of curvature of the bearing surface 73 of the first bearing 70A and the ratio of the radius of curvature of the second shaft end 66B with respect to the radius of curvature of the bearing surface 73 of the second bearing 70B may be set to equal to or less than 85% or equal to or less than 75%. In a case of such a configuration, gaps between the shaft ends 66 of the shaft 62 and the bearing surfaces 73 of the bearings 70 become suitable in size. Therefore, it is possible to suppress hemolysis from occurring due to sliding between the shaft 62 and the bearings 70.

In order to check a hemolysis suppressing effect obtained by setting the ratio of the radius of curvature, a test has been executed. In the test, in 15 mL of blood put in a container, while the shaft was pressed with a load of 40 N with respect to each of the bearings respectively corresponding to Samples B1 to B5 illustrated in FIGS. 8A to 8E, the shaft was continuously rotated for an hour at a rotational frequency of 3,000 rpm. In all the shafts used in the experiments, the outer diameter was 3.0 mm and the radius of curvature of the shaft end was 1.5 mm.

Figure 8A:
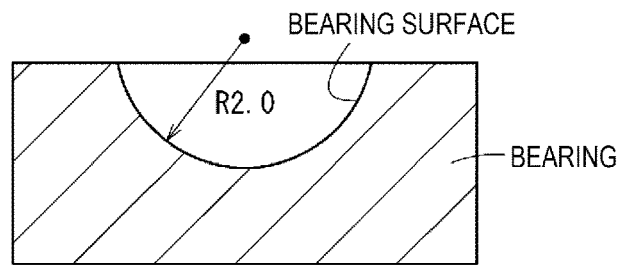
FIG. 8A is a cross-sectional view of a bearing according to Sample B1.
Figure 8B:
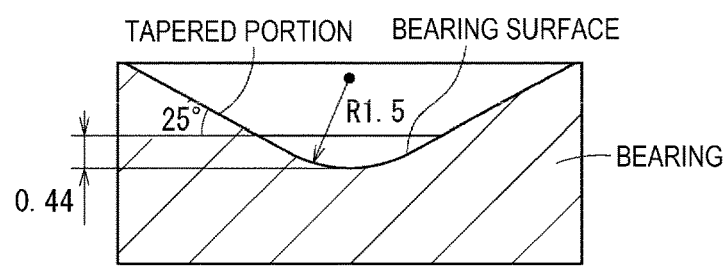
FIG. 8B is a cross-sectional view of a bearing according to Sample B2.
Figure 8C:
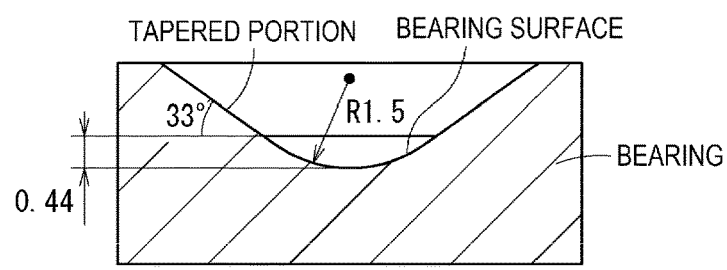
FIG. 8C is a cross-sectional view of a bearing according to Sample B3.
Figure 8D:
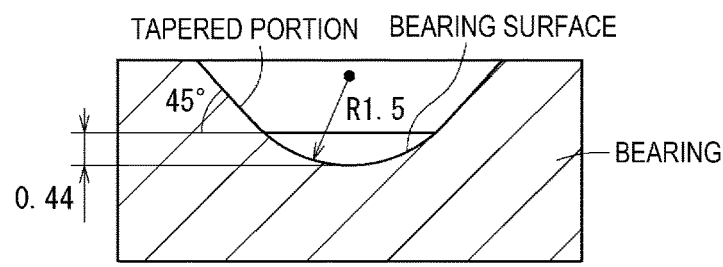
FIG. 8D is a cross-sectional view of a bearing according to Sample B4.
Figure 8E:
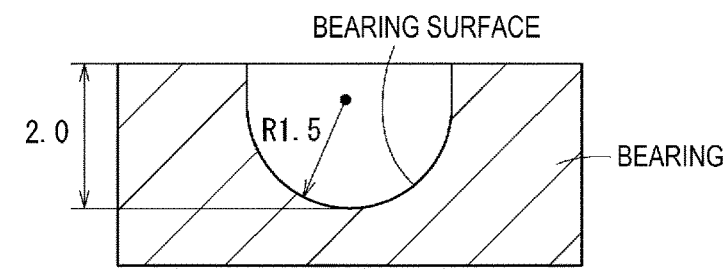
FIG. 8E is a cross-sectional view of a bearing according to Sample B5.

As illustrated in FIG. 8A, in the bearing of Sample B1, the radius of curvature of the bearing surface was 2.0 mm. Accordingly, the ratio of the radius of curvature of the shaft end of the shaft with respect to the radius of curvature of the bearing surface was 75%.

As illustrated in FIGS. 8B to 8E, in the bearings of Samples B2 to B5, the radius of curvature of the bearing surface was 1.5 mm. Accordingly, the ratio of the radius of curvature of the shaft end of the shaft with respect to the radius of curvature of the bearing surface was 100%. Note that, in Samples B2 to B4, the depth of the bearing surface was 0.44 mm which was smaller than the radius of curvature (1.5 mm) of the shaft end of the shaft. A tapered portion was provided on the periphery of the bearing surface. The angles of the tapered portion in Samples B2 to B4 were respectively 25°, 33°, and 45°. In addition, in Sample B5, the depth of the bearing surface was 2.0 mm which was greater than the radius of curvature of the shaft end of the shaft.

As a result of the test performed under the above-described conditions, hemolysis was effectively suppressed in Sample B1. Therefore, compared to Samples B2 to B5, it was confirmed that the amount of hemolysis was drastically small. It is considered that such a suppressing effect of hemolysis is achieved due to the gap retained in a suitably wide manner between the shaft end of the shaft and the bearing surface of the bearing.

Meanwhile, in Samples B2 to B4, as the angle of the tapered portion became smaller, that is, as the gap between the shaft and the bearing became greater, it was confirmed that the amount of hemolysis decreased. Nevertheless, the amount of hemolysis was greater than that of Example, and no particularly meaningful effect in terms of suppression of hemolysis suppression was observed. In Sample B5, it was confirmed that the amount of hemolysis increased remarkably. Regarding the case of Sample B5, it is considered to be caused by the fact that the bearing surface in its entirety contacts the shaft.

Figure 9A:
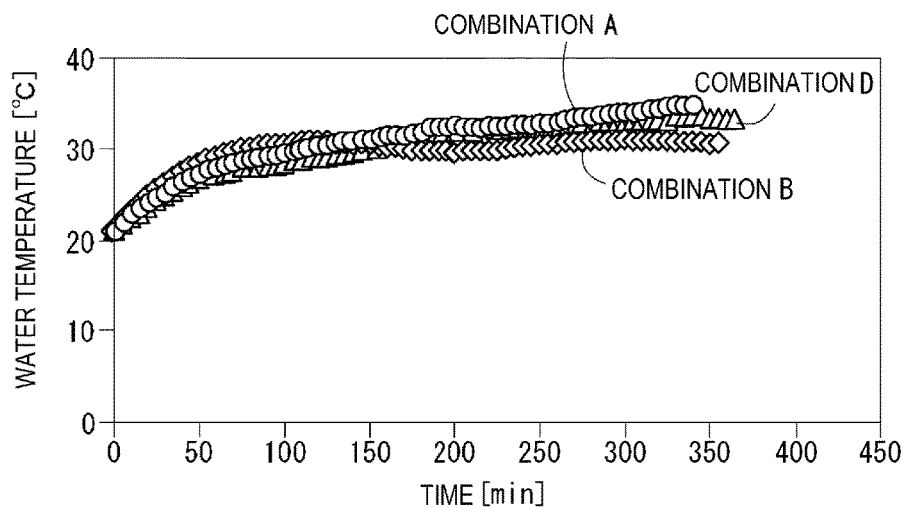
FIG. 9A is a graph illustrating an experimental result related to calorific values (i.e., heat generation) during rotations of a shaft.
Figure 9B:
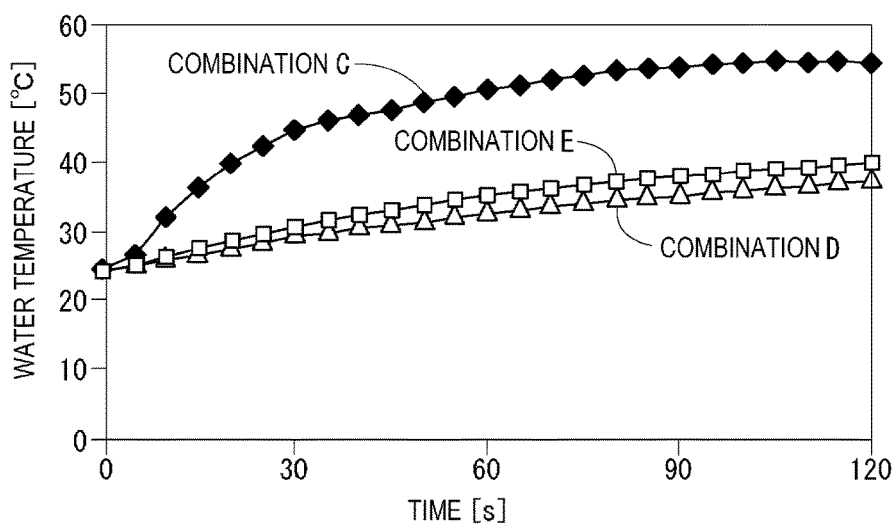
FIG. 9B is another graph illustrating the experimental result related to the calorific values during rotations of the shaft.

FIGS. 9A and 9B illustrate the experimental results related to the calorific values during rotations of the shaft, in each of the combinations (A to E) of the shafts and the bearings of which the radii of curvature are formed as shown in the following Table 2.

TABLE 2

| Combinations | Radius of Curvature of Shaft End of Shaft (mm) | Radius of Curvature of Bearing Surface (mm) | Ratio of Radius of Curvature (%) |
|---|---|---|---|
| A | 1.25 | 1.5 | Approximately 83 |
| B | 1.25 | 2.0 | Approximately 63 |
| C | 1.5 | 1.5 | 100 |
| D | 1.5 | 2.0 | 75 |
| E | 1.5 | 2.5 | 60 |

In this test, in 9 mL of fluid volume of water, while the shaft was pressed with a load of approximately 52 N (5.3 kgf) with respect to the bearing, the shaft was continuously rotated for a predetermined period of time at a rotational frequency of 2,500 rpm, and the temperature rise of water was measured. The room temperature was kept at 25° C. Note that, in Table 2, "Ratio of Radius of Curvature (%)" denotes the ratio (%) of the radius of curvature of the shaft end of the shaft with respect to the radius of curvature of the bearing surface.

As illustrated in FIGS. 9A and 9B, in the combination C, the temperature rise due to the elapse of time was significant, that is, the calorific value was great. In the combinations A, B, D, and E, compared to the combination C, a result of a gentle temperature rise due to the elapse of time, that is, a small calorific value was obtained. Incidentally, the combination C having a great calorific value corresponds to Sample B5 of FIG. 8E, and the combination D having a small calorific value corresponds to Sample B1 of FIG. 8A. From the above-referenced fact, it is considered that formation of hemolysis is greatly influenced by heat generation.

According to the test results thereof, in a case where the ratio of the radius of curvature of the shaft end of the shaft with respect to the radius of curvature of the bearing surface ranges from 60% to approximately 83%, it is ascertained that heat generation can be suppressed and a hemolysis suppressing effect can be obtained. In addition, from the fact that almost no difference was recognized between the calorific values (temperature rises) through the comparison between the ratio of 75% (combination D) and the ratio of approximately 83% (combination A), it is considered that even though the ratio is approximately 85%, a hemolysis suppressing effect can be obtained.

Note that, another experiment was performed so as to measure the amount of hemolysis with the combination of a flat bearing surface and a spherical surface-shaped shaft end, and the calorific value became the least in a case of this combination. From the above-referenced fact, even in a case where the ratio is less than 60%, it is ascertained that a hemolysis prevention effect can be obtained.

As it has been understood from the above-described fact, according to the present invention, when a relationship between the radius of curvature of the shaft end 66 of the shaft 62 and the radius of curvature of the bearing surface 73 of the bearings 70 (the ratio of the radius of curvature of the shaft end 66 with respect to the radius of curvature of the bearing surface 73) is set within a predetermined range (equal to or less than 85%), the gap between the shaft end 66 of the shaft 62 and the bearing surface 73 of the bearings 70 becomes suitable in size. Accordingly, it is possible to suppress hemolysis from occurring due to sliding between the shaft 62 and the bearings 70.

In addition, with reference to the experimental results, in addition to setting of the ratio related to the radius of curvature, when the radius of curvature of the shaft end 66 is set to range from 1.25 mm to 1.5 mm, or the radius of curvature of the bearing surface 73 is set to range from 1.5 mm to 2.5 mm, it is possible to effectively suppress hemolysis from occurring due to sliding between the shaft 62 and the bearings 70.

In addition, as is clear from the experimental results, when the radius of curvature of the first shaft end 66A (or the second shaft end 66B) is set to be 1.5 mm and the radius of curvature of the bearing surface 73 of the first bearing 70A (or the second bearing 70B) is set to be 2.0 mm, it is possible to reliably suppress hemolysis from occurring due to sliding between the shaft 62 and the bearings 70.

In addition, when the tightening load in the axial direction with respect to the shaft 62 is set to range from 30 N to 60 N, together with the above-described hemolysis suppressing effect obtained by setting the radius of curvature, it is possible to more effectively suppress hemolysis from being formed, and it is possible to suppress formation of a thrombus and damage to the bonded portion (an occurrence of a crack, and the like) between the base 48 of the housing 26 and the cover 50.

Note that, the ratio of the radius r1 of curvature of the first shaft end 66A with respect to the radius r2 of curvature of the bearing surface 73 of the first bearing 70A may be different from the ratio of the radius of curvature of the second shaft end 66B with respect to the radius of curvature of the bearing surface 73 of the second bearing 70B.

Therefore, for example, any one between the ratio of the radius r1 of curvature of the first shaft end 66A with respect to the radius r2 of curvature of the bearing surface 73 of the first bearing 70A and the ratio of the radius of curvature of the second shaft end 66B with respect to the radius of curvature of the bearing surface 73 of the second bearing 70B may be equal to or less than 85%. In this case as well, a hemolysis suppressing effect can be obtained.

In the above description, a preferred embodiment of the present invention has been exemplified. However, the present invention is not limited to the embodiment, and it is not necessary to mention that various modifications and changes can be made without departing from the scope of the present invention.

What is claimed is:

1. A centrifugal pump comprising:
a housing with opposing walls defining a pumping chamber, wherein one of the opposing walls includes a recessed receptacle;
an impeller rotatably disposed in the pumping chamber;
a shaft fixed to the impeller at a center rotational axis of the impeller and having opposing shaft ends;
bearing members on the housing walls pivotally supporting the opposing shaft ends, wherein the housing walls exert a tightening load on the shaft and bearing members, wherein one of the bearing members is disposed within the recessed receptacle; and
an elastic body which is elastically deformable in the axial direction of the shaft and which is disposed to transmit the tightening load between the housing walls, wherein the elastic body is disposed in the recessed receptacle between the one bearing member and the one of the opposing walls, wherein the elastic body has a base portion and a side wall, wherein the base portion deforms under the tightening load between the one bearing member and the one of the opposing walls, wherein the side wall surrounds an outer circumferential portion of the bearing member for elastically supporting the one bearing member in a radial direction.

2. The centrifugal pump according to claim 1 wherein the elastic body is made of silicone rubber.

* * * * *